(12) United States Patent
Brandimarte et al.

(10) Patent No.: US 12,432,510 B2
(45) Date of Patent: Sep. 30, 2025

(54) INTEGRATED CHEMICAL-PHYSICAL SYSTEM FOR TREATING TINNITUS

(71) Applicant: TINNITECH LTD, London (GB)

(72) Inventors: Bruno Brandimarte, Nettuno (IT); Gianantonio Pozzato, Vicenza (IT)

(73) Assignee: TINNITECH LTD, London (GB)

( * ) Notice: Subject to any disclaimer, the term of this patent is extended or adjusted under 35 U.S.C. 154(b) by 212 days.

(21) Appl. No.: 18/551,709

(22) PCT Filed: Mar. 23, 2022

(86) PCT No.: PCT/IB2022/052653
§ 371 (c)(1),
(2) Date: Sep. 21, 2023

(87) PCT Pub. No.: WO2022/201058
PCT Pub. Date: Sep. 29, 2022

(65) Prior Publication Data
US 2024/0179482 A1    May 30, 2024

(30) Foreign Application Priority Data

Mar. 24, 2021    (IT) .................. 102021000007154

(51) Int. Cl.
*A61N 1/40*    (2006.01)
*A61F 11/00*    (2022.01)
*H04R 25/00*    (2006.01)

(52) U.S. Cl.
CPC .................... *H04R 25/75* (2013.01)

(58) Field of Classification Search
CPC ............ H04R 25/75; A61N 1/40; A61F 11/00
USPC .................................................. 381/312, 328
See application file for complete search history.

(56) References Cited

FOREIGN PATENT DOCUMENTS

| EP | 3693053 A1 | 8/2020 |
|----|------------|--------|
| KR | 20140107768 A | 9/2014 |
| WO | 2011043678 A1 | 4/2011 |
| WO | 2018087645 A1 | 5/2018 |

OTHER PUBLICATIONS

International Search Report and Written Opinion for Corresponding International Application No. PCT/IB2022/052653, 9 pages, Jul. 25, 2022.

*Primary Examiner* — George C Monikang
(74) *Attorney, Agent, or Firm* — LUCAS & MERCANTI, LLP

(57) ABSTRACT

A device for applying an integrated therapeutic method for treating tinnitus is disclosed. The method provides the administration of noises, by means of the dedicated technical device, low-frequency and high-frequency electromagnetic waves, by means of the same device, and, if needed, oral functional-adjusting substances. Preferably, the method includes a biochemical step providing the administration of capsules or solutions by oral route and a physical step for administering acoustic signals and electromagnetic waves.

15 Claims, 1 Drawing Sheet

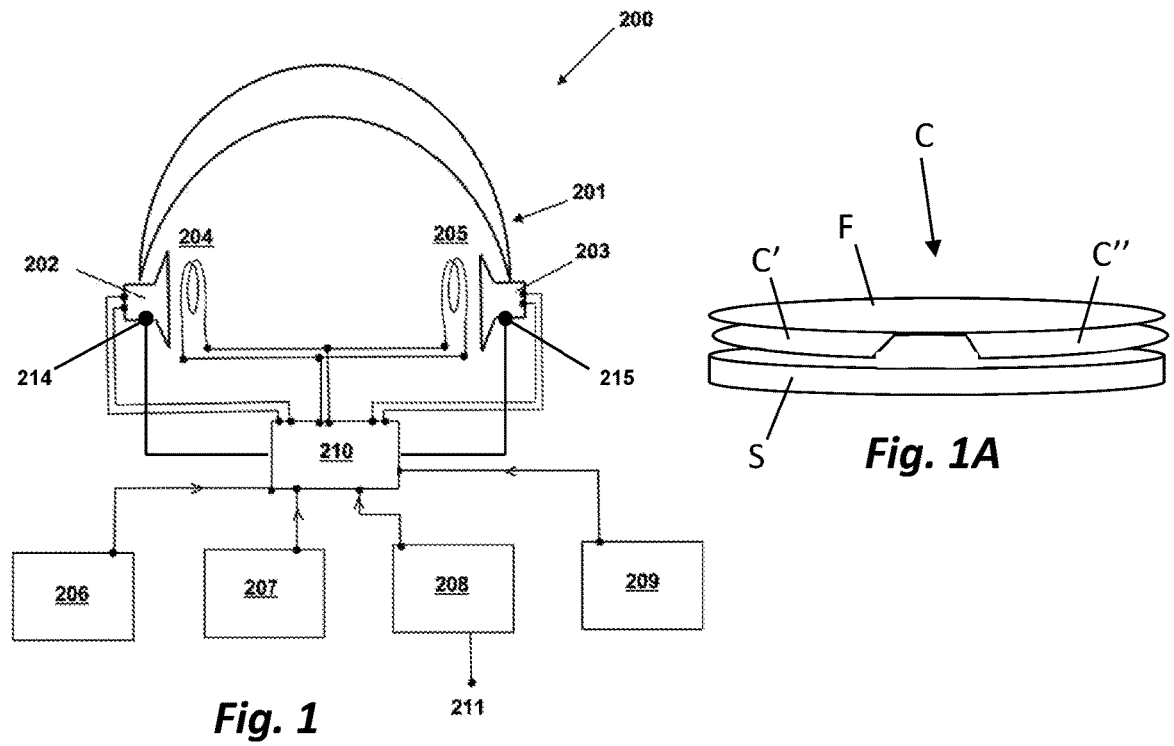
Fig. 1
Fig. 1A
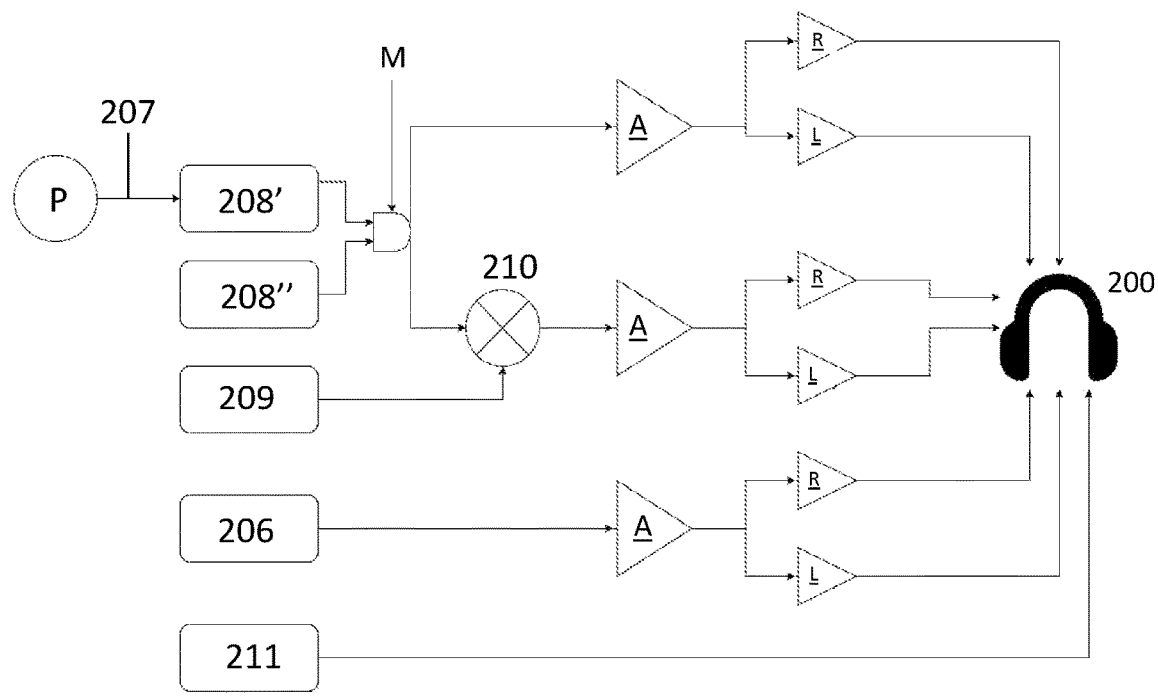
Fig. 2

INTEGRATED CHEMICAL-PHYSICAL SYSTEM FOR TREATING TINNITUS

CROSS-REFERENCE TO RELATED APPLICATIONS

This application is a 371 of PCT/IB2022/052653, filed Mar. 23, 2022, which claims the benefit of priority from Italian Patent Application No. 102021000007154, filed Mar. 24, 2021.

TECHNICAL FIELD OF THE INVENTION

The present invention relates to a device and to a composition for oral administration for treating tinnitus, further proposing a new integrated therapeutic method. The invention further relates to a treatment kit comprising said device and composition.

BACKGROUND

The term tinnitus designates the situation wherein a noise is perceived in one or both ears, or in the head, even if no sound is coming from outside. Tinnitus can be defined as a "perception of sounds in absence of physiological stimulation of the ear acoustic labyrinth" and it is caused by the abnormal stress of any area of the acoustic path, from the cochlea as far as the central brain areas located in the cortex.

Tinnitus, then, is wholly different from other noises which can be generated in the blood vessels, in the Eustachian tube, in the muscles or in the temporo-mandibular joint and which are transmitted through the skull bones. These noises can stimulate the ear in natural way and be perceived even by people other than the subject suffering therefrom. For this reason, such types of "sounds" are defined objective tinnitus, whereas the real tinnitus, called subjective tinnitus, can be heard only by the person complaining thereof.

The subjective tinnitus has mostly acute hue and it is often accompanied by hypoacusis (hearing loss). With the audiometric examination it is possible to determine the frequency of tinnitus (tinnitus examination). It is interesting to note that the tinnitus volume, if measured with laboratory instruments, is not related to the gravity of the tinnitus perceived by the same patients.

Tinnitus has different features depending upon the patient. For example, some people perceive the hearing disorder only immediately after exposure to very strong noises, such as for example after a concert. On the contrary, other subjects say to hear a feeble noise whenever they pay attention, but most of them cannot distinguish the noise from other environmental sounds.

Tinnitus is a symptom of a disease which can affect the ear (otogenic cause) or the whole organism (tinnitus by extra-otogenic cause).

The several causes which can produce tinnitus, many thereof are hardly to be ascertained, make it difficult to diagnose and treat the symptom, at the basis thereof it seems now established that there is a neural hyperexcitation.

A lot of therapeutic alternatives have been proposed and are still in use, each one thereof can give good results in single cases.

The medical therapy is based upon the use of vasodilators, anxiolytics and antidepressants (amitriptyline), herbal medicines (for example *Ginkgo biloba* extracts) or supplements.

The surgical therapy is based upon very demolitive operations, to be reserved for the most serious cases which deprive the patient of his/her hearing on the tinnitus side.

The physical therapy is based upon the fact of getting the patient used to hear relaxing sounds (sound-therapy) and of using particular acoustic prostheses, called maskers, which are capable, by emitting adequate sounds, to interfere with the tinnitus perception.

In selected cases, even the hyperbaric oxygen-therapy was used successfully, which is performed in the decompression chambers and which has the purpose of oxygenating and revitalizing the cells of the inner ear.

From the nutritional point of view, food capable of causing neuronal hyperexcitation is generally not recommended. Good therapeutic effects appear linked to:
- diet based on proteins by eliminating glycides and carbohydrates (metabolic ketosis),
- diets providing for the elimination of food capable of stimulating the release of histamine (for example salmon and tuna),
- diets based on taurine and glycine (they inhibit the neurons),
- diet based on purine (green vegetables, not alcoholic beer, allopurinol).

At last, even treatments of integrated type have been proposed, of the type described in WO2018/087645A1, providing the use of apparatuses configured to deliver suitable (acoustic and/or electromagnetic) signals at the patient's auditory system and in combination with the administration of functional-regulating substances for the organism.

However, despite tinnitus is an extremely widespread disorder, with a not negligible social impact, really effective and versatile technical systems and therapies have not yet been detected, neither for an independent use nor of integrated type, in particular modular upon the needs of the specific patient. Moreover, in-use systems and therapies do not succeed in obtaining a significant time duration of the beneficial effects of reduction or latency of the disorder, since such effects cease soon after the removal of the delivering apparatuses (for example headphones).

SUMMARY OF THE INVENTION

The technical problem placed and solved by present invention is then to provide an integrated therapeutic system, in particular based upon the use of a technical device, preferably but not necessarily, combined with an administration of substances capable of obviating the above-mentioned drawbacks and limits with reference to the known art.

Such problem is solved by a device according to claim 1.

Preferred features of the present invention are set forth in the depending claims.

In the present context, under "acoustic signal" a simple or complex combination of sound waves or a sound, of any duration is meant.

The invention is based upon a therapeutic method of integrated type for treating tinnitus.

In particular, the device of the present invention allows to treat tinnitus by obtaining on the patient a significant time duration of the beneficial effects of reduction or latency of the same disorder.

Such method provides the administration of:
- sounds;
- suitably quantized low-frequency electromagnetic waves;
- high-frequency electromagnetic waves supplied at the cochlea, in particular the area of the organ of *Corti*.
- in case, selected functional-regulating substances, by oral route.

The sounds and, both high-frequency and low-frequency, electromagnetic waves are administered to the patient preferably by means of one single dedicated technical device.

In particular, preferably but not necessarily, said method comprises a biochemical step, providing the administration of capsules or solutions by oral route, advantageously according to a dosage and posology pre-established to synergize the various active principles, the latter preferably of natural origin.

As said above, the method further comprises an analytical/delivering step for administering high and low-frequency sounds and electromagnetic waves, preferably by means of the same dedicated technical device.

Preferably, such device comprises a dispenser "headphone" and a programmable control unit allowing the operator (otolaryngologist or audiometrist) or the patient to customize the treatment to better adapt to the peculiarities of the disease and to the real therapeutic needs of the patient himself/herself.

In a preferred embodiment thereof, the proposed method then provides to integrate six distinct therapeutic interventions:
otometric analysis of the disorder;
preparation of the therapeutic programme;
administration of sounds;
administration of low-frequency electromagnetic waves;
administration of high-frequency electromagnetic waves;
a possible administration of substances by oral route.

Other advantages, features and use modes of the present invention will result evident from the following detailed description of some embodiments, shown by way of example and not with limitative purposes.

BRIEF DESCRIPTION OF FIGURES

The figures of the enclosed drawings will be referred to, wherein:

FIG. 1 shows a schematic representation of a technical device for the administration of sounds and low- and high-frequency electromagnetic waves according to a preferred embodiment of the invention, preferably intended for use in a same treatment of tinnitus with a composition for oral administration according to the invention;

FIG. 1A shows a preferred embodiment of the capacitive means for the electromagnetic stimulation implemented in the device of the invention;

FIG. 2 shows a block diagram of circuit design of a preferred embodiment of the acoustic/electromagnetic device shown in FIG. 1.

DETAILED DESCRIPTION OF PREFERRED EMBODIMENTS

By firstly referring to FIG. 1, a device for the administration/acoustic and electromagnetic stimulation according to the invention, designated as a whole with 200, is described.

A preferred embodiment of such device, in particular a schematic view of the block circuit diagram which the device implements, is shown in FIG. 2.

The device 200 comprises a wearable support 201, preferably in form of headset.

The device 200 comprises a pair of acoustic dispensers, or emitters, connected to the support 201. In particular, a right dispenser 202 and a left dispenser 203 are provided, each one adapted to administer acoustic signals at the respective auricles and suitably shaped to this purpose. The dispensers 202 and 203 can be connected to the support 201 so as to result fixed or movable according to one or more degrees of freedom, and in case removably.

At or near each dispenser 202, 203 electromagnetic stimulation means is further provided, which will be described in details hereinafter.

The emitters 202 and 203 and the electromagnetic stimulation means are preferably connected to additional units of the device 200, preferably to a unit 210 mixing the signals which provides directly the acoustic and electric signals, respectively, to such emitters and electromagnetic stimulation means. The mixing unit 210 can even provide for their relative energy supply.

The mixing unit 210, in turn, is in, preferably bidirectional, communication with one or more additional components of the device 200, described hereinafter.

Preferably, a control unit (not shown in Figures) is provided, configured to process a programming acoustic signal. Such signal is determined through an audiometric examination to determine frequency and intensity of the tinnitus disorder, and the control unit is configured to control a first acoustic generator 207 so that the latter delivers a main acoustic signal, which will be called treatment signal, suitable to contrast the tinnitus perception.

Preferably, the treatment acoustic signal associated to the generator 207 is delivered by the emitters 202 and 203 through the mixing unit 210.

In particular, the control unit stores and processes the data obtained with the audiometric examination and uses them to program the generator 207 of treatment acoustic signals. The control unit and/or other components of the device 200 are preferably provided with means for measuring and/or determining the frequency and intensity of both acoustic and electromagnetic signals.

The generator 207, through the dispensers 202 and 203, administers to the subject said treatment acoustic signal which, preferably, has the same features, in terms of frequency and intensity, of the programming acoustic signal determined with the audiometric examination or a (partially) different acoustic signal.

Preferably, the treatment acoustic signal administered to the subject and associated to the generator 207 is mixed (or modulated) with a secondary acoustic signal (or sub-signal), such as for example notes, music, noise, such as white noise or the like.

To this purpose, the device 200 provides a second generator of acoustic signals, or an auxiliary generator designated with reference 208, in communication with the mixing unit 210.

Said auxiliary generator 208 is configured to deliver a secondary acoustic signal, in particular sounds from the sub-sound to the ultrasounds.

Such secondary acoustic signal preferably is sinusoidal and has a frequency comprised between approximatively 5 Hz (sub sound) and approximatively 20 kHz (ultrasound threshold), which secondary acoustic signal can be suitably selected by an operator both in frequency and in intensity based upon the type of application to be performed. The operator then could search for, select and store for example one or more suitable frequencies (and corresponding intensities) of the second acoustic signal.

The auxiliary acoustic generator 208 is preferably provided with, or associated to, a control panel for controlling and regulating the secondary acoustic signals to be delivered. In preferred embodiments, the auxiliary acoustic generator 208 comprises internal storage means.

In a preferred embodiment, the secondary acoustic signal is mixed to the main acoustic signal provided by the generator 207 through the mixing unit 210. Subsequently, the so-mixed signal is administered as treatment acoustic signal to the subject through the emitters 202, 203.

Advantageously, through the dispensers 202 and 203 a second acoustic signal comprised between 5 Hz (sub-sound) and 20 kHz (ultrasound threshold) can then be provided, separately or in conjunction with the above-mentioned main treatment acoustic signal.

In embodiments, the second acoustic signal can have a function modulating the main acoustic signal obtained through the first acoustic generator 207.

In additional embodiments, the secondary acoustic signal can be pre-stored in the generator 208 or provided through an auxiliary input 211 connecting it to data banks or external generators of musical signals, noise or other acoustic signals (musicotherapy).

In the example of FIG. 1, the auxiliary acoustic generator 208 can be configured as amplifier of the acoustic signal provided with the auxiliary input 211.

The device 200 preferably comprises suitable electronic components to manage acoustic signals of different nature or origin, such as for example amplifiers, analogue-to-digital converters, audiometric measurers, multiplexers or the like, generally designated with reference A in FIG. 2.

The control unit preferably is in bidirectional communication with all units and components of the device itself.

As anticipated, the device 200 further comprises electromagnetic stimulation means, in particular inductive means and capacitive means.

The electromagnetic stimulation means of inductive type comprises a respective signal generator, designated in Figures with reference 209 and, preferably, an inductor solenoid 204, 205 at or near each dispenser 202, 203.

In a preferred embodiment, each inductor solenoid 204, 205 consists of a winding of enameled copper wire, in particular with section comprised in a range of 0.2-0.4 mm and, for example, with a number of turns comprised between 20 and 100, so as to create an electromagnetic field suitable to generate electro-induction of micro-electric signals in the inner area of the ear and at the acoustic nerve.

According to an embodiment, the acoustic signal obtained by means of one or more of the acoustic generators 207, 208 is sent to electromagnetic stimulation inductive means 204 and 205 by means of said control unit and, in case, of the mixing unit 210. The control unit processes/translates the received signal and provides a corresponding control to the electromagnetic stimulation inductive means 204 and 205.

The electromagnetic stimulation inductive means 204, 205 deliver first electromagnetic signals capable of inducing in the area of the acoustic nerve a micro-electric stimulation which causes a light hyperemia and interferes with the transmission of the disorder to the brain.

Such micro-electric signals induced on the acoustic nerve allow to activate at cellular level, through the delivery of athermal energy, the transformation of ATP into ADP with relative request for oxygen (by micro-blood route) and reduce, on the electric nerve transmission, the electric space available to the disorder signal.

The capacitive means is configured to deliver a second electromagnetic signal at the cochlea, in particular of organ of Corti. The electromagnetic stimulation capacitive means comprises a capacitive emitter 214, 215 at each one of said dispensers 202, 203.

Preferably, the electromagnetic stimulation capacitive means is carried by the support 201 of the device 200 so as to result to be positioned, in use, at the organ of Corti.

In particular, said electromagnetic stimulation capacitive means is placed in the support 201 and is configured to emit signals at the organ of Corti and of the whole cochlear area, the organ of Corti being situated in the central area of the cochlea.

In addition to the previously described electromagnetic stimulation, obtained by inductive route, the electromagnetic stimulation capacitive means allows to deliver second and additional high-frequency electromagnetic signals, in particular radiofrequency signals, preferably signals at a frequency comprised between 1 MHz and 100 MHz.

Said high-frequency electromagnetic signals can be configured so as to contain both a main signal, designated "fundamental", and secondary signals with different frequencies designated "harmonic". For example, such harmonics provide frequencies comprised between 2 MHz and 100 MHz, to be delivered simultaneously to the fundamental signal and with gradually decreasing width.

In a preferred embodiment, as illustrated in the example in FIG. 1A, said electromagnetic stimulation capacitive means 214, 215 comprises a condenser C implemented through a pair of conducting elements C', C". Preferably, at each acoustic emitter 202, 203 there is a condenser C.

The conducting elements C', C" are insulated therebetween and with respect to the exterior of the device 200, in particular with respect to the skin of the patient wearing it, so as to constitute a conductor-insulator-conductor configuration typical of a condenser.

Preferably, each conducting element is implemented in the form of a plate-like element—or plate or armour—shaped substantially like a semicircle. Advantageously an implementation with reduced overall dimensions is then possible, in particular inside the structure of the pavilions of the device 200.

According to a preferred embodiment, said conducting elements C', C" have a multi-layer structure and can be obtained starting from a printed circuit.

The conducting elements C', C" are made of electrically conductive material and they are spaced apart therebetween, for example by a distance equal to about 5 mm.

The conducting elements C', C" are preferably applied on a support, or substrate, S with planar sizes preferably lower or equal to 40 mm. The stimulation capacitive means 214, 215 can be coated with insulating means, for example a layer of paint for printed circuits.

According to a preferred embodiment, the insulating means comprises a sheet F made of insulating material, applied to said layer of paint, if present. Said sheet F preferably has a thickness in the order of the tenth of a millimetre. The thickness of the sheet F can be selected depending upon the value in Volts corresponding to the (radio)frequency therewith the electromagnetic signal will be delivered by the capacitive emitter.

Preferably, the conducting elements C', C" are incorporated in the device 200 so that the insulating means, in particular said insulating sheet F, results to be faced towards the patient under condition of worn device.

Each capacitive emitter 214, 215, in particular each pair of conducting elements C', C", is connected to a radiofrequency signal generator, designated in FIG. 1 with reference 206.

The radiofrequency signal generator sends the signal to the capacitive emitters 214, 215 by means of said control unit and, preferably, the mixing unit 210.

In particular, each capacitive emitter 214, 215, or each pair of conducting elements constituting them result, in use, to be positioned at the organ of *Corti* of the patient wearing the device.

Advantageously, the electromagnetic stimulation capacitive means is configured to deliver second high-frequency electromagnetic signals, and preferably with low intensity, for example with intensities comprised between 5 mW (milliwatt) and 50 mW (milliwatt).

The second electromagnetic signals obtained by capacitive route are capable of reducing a possible hyperexcitation or possible inflammation of the vibratile cells constituting the organ of *Corti* or other portions of the cochlear area, the organ of *Corti* being positioned in the centre of the cochlear area, by producing the effect of de-exciting them, thus reducing their capability of generating electric signals which are at the origin of the tinnitus disorder.

Come anticipated, the control unit can be provided as common, that is shared, component for the different generators, units and elements mentioned sofar. Preferably, the control unit is of microprocessor type.

Moreover, the above-mentioned units and generators, although described as structurally distinct, are advantageously incorporated in a same multifunction device.

Therefore, during a typical use of the device, the programming acoustic signal is determined based upon tests performed on the patient through an audiometric examination which identifies the intensity and the frequency of tinnitus. Once such determination has been performed, the treatment signal to be delivered is developed, which in case can be stored in the acoustic generators 207, 208 and stably used.

Advantageously, the treatment signal provides a main acoustic signal in combination with additional acoustic signals and/or electromagnetic signals.

The features of the treatment signal—in particular the frequency of the modulated signal and of the modulating one for the electromagnetic portion of the stimulation—could be established in a first treatment session, by testing on the patient the feeling of reducing the tinnitus noise.

With reference to the embodiment of the device illustrated in FIG. 2, contemporarily to the delivery of the acoustic signal, the electromagnetic stimulation inductive means could deliver first electromagnetic signals the frequency thereof varies preferably between 1 kHz and 30 kHz.

For example, an operator can select through a control panel P the frequency and/or the intensity of the main acoustic signal generated by the means 207.

The main acoustic signal could be mixed (or modulated) with a secondary acoustic signal 208' and/or 208", for example with an acoustic signal equal to the fundamental +10%, to the fundamental −10% or even white noise. Means M for selecting the type of modulating acoustic signal is preferably provided.

The so-obtained mixed (or modulated) acoustic signal could be sent to the acoustic emitters 202, 203 and/or processed by the mixing unit 210 in turn acting as modulating signal for the electromagnetic signal associated to the inductive means and generated by the generator 209.

Frequencies (and/or intensities) of the electromagnetic signal of inductive type can be used, for example test frequencies equal to 5 kHz, 10 KHz and gradually by attempts up to 30 KHz.

Although not illustrated in FIG. 2, an analogous procedure can even be applied, alternatively or in combination, with the electromagnetic stimulation capacitive means, in particular by modulating the signal selected with the signal of the radiofrequency generator 206.

The best frequency could be selected, which could even be confirmed in a second session.

The acoustic and/or electromagnetic signal administered to the subject respectively with the emitters 202, 203 and with the electromagnetic stimulation inductive means 204, 205 and/or capacitive means 214, 215 could have different features with reference to the right or left auricle, or be administered at one only auricle, depending upon the features of the disorder detected during the diagnosis step.

In FIG. 2 the blocks designated with reference R and L show the possibility of selecting independently or jointly the right or left channel of the device 200 for each type of treatment (or programming) (acoustic/electromagnetic) signal to be delivered.

Advantageously, the whole device 200—including the above-illustrated acoustic emitters 202-203, stimulation inductive means 204-205, stimulation capacitive means 214, 215, generators and units 206-211—is entirely wearable, that is such generators and units are arranged on the support 201 or on different transportable base which can be applied on the patient body.

The device 200 can be self-powered by means of, in case rechargeable, batteries, and/or it can be connected to an external energy source. The battery depletion can be signalled, for example on the control panel, to allow the activation of the connection with the battery charger.

In the preferred embodiment thereof, the device 200 comprises bidirectional communication means configured to establish a connection between said device and a control and programming system. Such bidirectional communication means allows to transmit and/or store data from/towards the device 200 and the remote programming of the latter.

Advantageously, such connection is a, preferably wireless, network connection and the bidirectional communication means comprises an operating system provided with a user interface for the device (200) connected, in use, with an operator interface intended to be implemented by the control and programming system.

For example, the device 200 is provided with an electronic system and with multiple technologies for the network connectivity including an interface for the patient and a direct, or via i-cloud, interface for the physician, aiming at the transmission and storage of data, as well as the programmability of the system and of the clinical treatment with the relative parameters and the operating and health instructions remotely, through ports of various nature including USB, ethernet and wifi. Such ability of operating in remote connectivity allows a check and an authorization for locking and unlocking the operation, reading and storing the instructions and the authorizations given to the patient which guarantee to obtain a treatment faithful to original medical dictates, as well as of diagnostic/therapeutic health service which according to the guidelines of the national and International health authorities qualifies as come telemedicine.

In summary, the physical portion of the method develops its action according to the main steps shown hereinafter.

Determination of the signal which generates tinnitus through method of audiometric analysis (to define apart from the frequency even the intensity of the disorder), performed internally in the so-enabled versions of the device or, alternatively, with external measurers.

Administration to the subject of acoustic signals corresponding to the disorder, in case mixed with additional acoustic signals which can compress and reduce the transmission of the disorder signal to the brain.

Induction in the area of the acoustic nerve of low-frequency microelectric signals through electromagnetic stimulation means of inductive type which cause a light hyperemia and which, by occupying the neural transmission, interfere with the transmission of the disorder to the brain.

Administration in the area of the organ of *Corti* of high-frequency electromagnetic signals through electromagnetic stimulation means of capacitive type which reduce the hyperexcitation and possible inflammation of the vibratile cells which constitute the organ of *Corti* and interfere with the transmission of the disorder to the brain.

Preferably, the above-mentioned steps are synchronous with the administration of active principles administered by oral route and described hereinafter.

The composition for oral administration can include one or more of the following active ingredients: vitamin B1, vitamin B6, vitamin B12, Lithium Orotate, Magnesium, Ginger, Hawthorn and lemon balm.

Examples of concentration of said active ingredients per dosage unit to be used in the compositions are:
vitamin B1 between 5 mg and 50 mg, preferably 25 mg;
vitamin B6 between 0.5 and 2 mg, preferably 1 mg;
vitamin B12 between 0.5 mg and 2 mg, preferably 1 mg;
Lithium orotate between 0.5 mg and 2 mg, preferably 1 mg;
Magnesium between 100 mg and 500 mg, preferably 300 mg;
Ginger between 500 mg and 1000 mg, preferably 700 mg;
Hawthorn between 400 mg and 1200 mg, preferably 600 mg;
Lemon balm *officinalis* between 600 mg and 1200 mg, preferably 900 mg.

In a preferred embodiment the composition will include as active ingredients vitamin B1, vitamin B6, vitamin B12, Lithium orotate, Magnesium, Ginger, an extract of Hawthorn and of Lemon balm *officinalis*.

In an embodiment in the compositions as hawthorn an extract of extract of leaves and flowers of the species *Crataegus monogyna* Jacq will be used, in particular an extract of leaves and flowers and powder of dried fruits in the ratio 1:2 and/or an extract of dried leaves of Lemon balm *officinalis*.

The compositions for example could be formulations such as capsules, soft capsules, tablets, pills, jellies, powders or granules, solution, suspension and comprise one or more excipients. Such excipients can be selected for example among those usually known in the state of art and include, but they are not limited thereto: a) carriers, such as for example sodium citrate and calcium phosphate, b) fillers, such as for example starch, lactose, microcrystalline cellulose, sucrose, glucose, mannitol and colloidal silica, c) wetting agents, such as for example glycerol, d) disintegrating agents, such as alginates, calcium carbonate, starches, derivatives of starch, of cellulose and of polyvinylpyrrolidone, silicates and sodium carbonate e) binders such as carboxymethylcellulose, alginates, gelatine, polyvinylpyrrolidone, sucrose, polymeric derivatives of cellulose, starch derivatives f) retarding agents such as paraffin, cellulose polymers, esters of fatty acids g) absorption accelerators, such as compounds of quaternary ammonium, h) wetting agents and surfactants such as cetyl alcohol and monostearate glycerol, i) adsorbents, such as Benthic clays and kaolin, k) lubricants such as talcum, calcium stearate, magnesium stearate, polyethylene glycol, sodium lauryl sulfate, sodium stearyl fumarate j) glidants such as talcum, colloidal silica.

The forms of solid dosage, such as tablets, capsules, soft capsules, jellies, pills and granules, could be coated with enteric, gastric coatings or of other type known in the state of art. They can include matting agents and can be of the type to allow the release of the active ingredients only or preferably in a certain tract of the intestine, in case in delayed way. Substances which can allow such delayed use include, but they are not limited thereto, polymers and waxes.

The compositions will be for example a medical device, a dietary supplement, a nutraceutical, dietary and nutritional composition, a food product, a beverage, a nutraceutical, a medicament, medicated food, food for special medical purposes, food. The combination of the above-mentioned active ingredients could be used formulated in one single composition according to the various above-described embodiments or in a kit including the different separate ingredients, for example in single compositions such as capsule, pills, lozenges for sequential or contemporary administration of the different ingredients.

The above-described compositions are for use as medicament, in particular in a method for the prevention and/or treatment of tinnitus. Preferably in a treatment method wherein said composition is administered at least once a day.

In an embodiment, the present invention provides for the use of the herein described compositions in a treatment method in a subject suffering from tinnitus, wherein said treatment method provides that said subject wears a device according to any one of the herein described forms.

Experimentally in fact it was found that the patients in relaxing state are more receptive to the previously described method, and at this point it will be better understood that the proposed system and method can provide advantageously, but not necessarily, the synchronized use of pharmacological principles, preferably of phytotherapy origin, with synchronous function for gastrointestinal intake. Such principles, with their both anti-inflammatory and circulatory as well relaxing action, prepare the auditory organ and its transmission system to the targeted action of the physical means guided by the audiometric analysis step.

The overall therapeutic system is clearly synergic, contrary to the currently used methods which result to be applied in a separate and random way as well as with much more limited and partial action.

In particular, the proposed system and method overcome the problems of the known solutions, which are mainly addressed to the use of masking and conditioning acoustic signals to increase the tolerability of the disorder, and allows a specific action of reduction and disappearance of tinnitus for a duration of several hours or even days by also showing a cumulative effect with the increase in the progressive reduction of the disorder with the subsequent delivery of the treatment sessions.

Advantageously, in the clinical practice the method allowed by the invention is associated to a counselling preliminary step which probes, in particular, all possibilities and helps the patient with thorough explanations about the symptoms and the possible therapies.

Preferably, the diagnosis is formulated by means of the specialist examination completed by instrumental assessments aimed at verifying the ear, in particular audiometry, tinnitus examination, impedancemetry, ABR, and by other checks of various type adapted to diagnose secondary tinnitus to extra-otogenic causes: blood examinations, Ecg, Holter Ecg and blood pressure, Eco-doppler TSA, X rays, electroencephalogram (EEG), magnetic resonance (MR) and others.

Based upon an additional aspect of the invention, then a method for the treatment of a patient with the tinnitus disorder is provided, comprising, preferably but not necessarily, a step of administration to said patient an oral composition as described above and an additional step of administration of sounds and electromagnetic waves, preferably by means of the above-described device.

According to a preferred embodiment, the treatment method comprises the steps illustrated hereinafter.

At first, the intake of a capsule or a solution by oral route is provided. Preferably the intake will follow this protocol: in the morning, for example before breakfast. After intake, for example after at least 30 minutes, one will proceed with a first control session and articulated programming as illustrated hereinafter.

With the acoustic generator 207 the frequencies and the intensities of the tinnitus disorder are searched for, the latter are quantified singularly in db, and a (paper or electronic) table is filled in—displayed for example on a control panel of the device 200—which shows a correspondence of the type: $F_1$ (Hz), $B_1$ (db); $F_2$ (Hz), $B_2$ (db); and so on depending upon the number of pairs of frequencies/intensities associated to the tinnitus disorder.

With the obtained data the acoustic generator 207 and in case the auxiliary acoustic generator 208 will be (re)programmed.

For example, the treatment acoustic signal emitted by the acoustic generator 207 will be programmed (preferably automatically by means of an "enter" button), which signal—as said—in case could be mixed with the secondary acoustic signal (sub-signal or external signal) generated by the auxiliary generator 208 or provided with the auxiliary input 211.

Once performed the (even audiometric) measuring, verifying and programming step mentioned above, one will proceed with delivering the treatment acoustic signals and/or treatment electromagnetic signals.

Through the electromagnetic stimulation inductive means 204, 205 of the headphones 200, one will administer to the subject, for example, a first electromagnetic signal in subsequent frequencies, preferably comprised between 1 kHz and 30 kHz, in case modulated with the signals associated to the generators of acoustic signals 207 and/or 208.

Preferably, the stimulation inductive means will deliver an electromagnetic signal for an application time preferably comprised between 15 and 30 minutes.

Contemporarily, the electromagnetic stimulation capacitive means 214, 215 will deliver a high frequency, in particular radiofrequency, electromagnetic signal, preferably through the condenser C. The capacitive means will deliver said electromagnetic signal at the organ of *Corti* and of the surrounding areas belonging to the cochlear areas, the organ of *Corti* being positioned in the centre of the cochlear area, and preferably adjusted so that the patient feels a slight heat in this region.

Once the above-mentioned application time has elapsed, a control on the disorder situation will be performed.

At the end of the session and of the control, the automatic portable apparatus will be entrusted to the patient, which apparatus is programmed to deliver as determined in the previous step and which will have to be used preferably in the morning for a treatment time comprised between 15 and 30 minutes.

Preferably, after about seven days from the initial session, one will proceed to fill in a module mentioning the main parameters to verify the effectiveness of the programming and in case one will adjust the automatic programming of the apparatus supplied to the patient.

Subsequently the module could be filled in weekly and in case a second module even fortnightly with additional evaluation parameters.

A control session after 30 treatment days will allow a first evaluation of the effectiveness of the treatment itself.

As said, advantageously the method is performed by means of a same programmable device to be used in the office of the preliminary session which will be then entrusted to the patient for the home use. Preferably, the device of the invention could not be modified in programming by the patient himself/herself.

The present invention has been so far described with reference to preferred embodiments. It is to be meant that other embodiments belonging to the same inventive core may exist, as defined by the protective scope of the herebelow reported claims.

The invention claimed is:

1. An acoustic device configured for the treatment of tinnitus, which acoustic device comprises:
   a wearable support (201), substantially in the form of headset;
   an acoustic signal generator, configured to deliver a treatment acoustic signal;
   a pair of acoustic emitters connected to said acoustic signal generator, wherein each acoustic emitter is arranged on said wearable support in such a way as to be positioned, in use, at a respective auricle of a user;
   an electromagnetic signals generator, configured to deliver an electromagnetic signal of treatment and comprising first inductive stimulation component and second capacitive stimulating component carried by said support in such a way as to be positioned, in use, at or in proximity of the user's auricles,
   wherein said first inductive component is configured to deliver a first electromagnetic signal in the area of the acoustic nerve and wherein said second capacitive component is configured to deliver a second electromagnetic signal at the cochlear area, at the organ of Corti.

2. The acoustic device according to claim 1, wherein said second capacitive stimulating component is configured to deliver a radio frequency second electromagnetic signal.

3. The acoustic device according to claim 2, wherein the radio frequency second electromagnetic signal comprises a main signal and one or more secondary signals, wherein said one or more secondary signals have frequencies between 2 MHz and 100 MHz, and said one or more secondary signals are delivered simultaneously with the main signal and have progressively decreasing width.

4. The acoustic device according to claim 1, wherein said second capacitive stimulating component comprises a capacitor formed by a pair of plate-like elements having a semicircle shape.

5. The acoustic device according to claim 1, wherein said capacitive component is coated with insulating material having a thickness proportional to the frequency of the second electromagnetic signal to be delivered.

6. The acoustic device according to claim 1, wherein said first inductive stimulating component is configured to deliver the first electromagnetic signal at a frequency comprised between 1 kHz and 30 kHz.

7. The acoustic device according to claim 1, further comprising a mixing unit (210)-configured to receive two or more input acoustic signals from said acoustic signal generator and to deliver said treatment acoustic signal.

8. The acoustic device according to claim 1, wherein said acoustic signal generator is configured to deliver a treatment acoustic signal with variable frequency.

9. The acoustic device (200) according to claim 1, wherein said acoustic signal generator comprises an auxiliary acoustic generator configured to generate a secondary acoustic signal with a frequency of between 5 Hz and 20 kHz.

10. The acoustic device according to claim 1, wherein said acoustic signal generator and/or said electromagnetic signals generator comprise storage means.

11. The acoustic device according to claim 1, wherein said acoustic signal generator is configured to be connected with a signal database external to the device.

12. The acoustic device according to claim 1, further comprising a bidirectional communication unit configured to establish a connection between said device and a control and programming system configured to transmit and/or store data and to remotely program the device itself.

13. The acoustic device according to claim 12, wherein said connection is a wireless network connection and the bidirectional communication unit comprises an operating system provided with a user interface for the device connected, in use, with an operator interface intended to be implemented by the control and programming system.

14. A kit for the treatment of tinnitus comprising a device according to claims 1 and a composition for oral administration.

15. The acoustic device according to claim 2, wherein said second capacitive stimulating component is configured to deliver a radio frequency second electromagnetic signal at a frequency of between 1 MHz and 100 MHz.

\* \* \* \* \*